United States Patent [19]
Pagliolo et al.

[11] Patent Number: 5,088,490
[45] Date of Patent: Feb. 18, 1992

[54] BANDPASS FILTER CLOCK CONTROL

[75] Inventors: Joseph P. Pagliolo, Columbia Heights; Russell E. Anderson, Brooklyn Park; Richard F. Weispfenning; Robert A. Betzold, both of Fridley, all of Minn.

[73] Assignee: Medtronic, Inc., Minneapolis, Minn.

[21] Appl. No.: 467,591

[22] Filed: Jan. 19, 1990

[51] Int. Cl.$^5$ .............................................. A61N 1/36
[52] U.S. Cl. .............................. 128/419 PG; 307/521
[58] Field of Search ................ 128/419 PG; 333/173, 333/18; 330/107, 109; 307/521

[56] References Cited

U.S. PATENT DOCUMENTS

| | | | |
|---|---|---|---|
| 4,665,919 | 5/1987 | Mensink et al. | 128/419 PG |
| 4,702,253 | 10/1987 | Nappholz et al. | 128/419 PG |
| 4,913,145 | 4/1990 | Stotts | 128/419 PG |
| 4,967,747 | 11/1990 | Carroll et al. | 128/419 D |

Primary Examiner—William E. Kamm
Assistant Examiner—Kennedy J. Schaetzle
Attorney, Agent, or Firm—Reed A. Duthler

[57] ABSTRACT

A switched capacitor ventricular sense amplifier for an implantable pulse generator having unique control of the switching clock for minimization of transients during the period just preceding, during and following an atrial paced event. The timing is modified to discontinue switching during this period. This ensures that transients occurring as a result of functionally disconnecting and subsequently reconnecting the sensing lead with the sense amplifier are not propagated within the switched capacitor bandpass filter. An alternative approach is to increase the clocking rate during the blanked period to ensure that the transients created by the atrial pace or by disconnecting and reconnecting the sensing lead are rapidly processed by the switched capacitor bandpass filter and that processing is completed shortly following the atrial paced event. This alternative approach requires a gate at the sense amplifier output to disable propagation of any transients processed.

6 Claims, 9 Drawing Sheets

BANDPASS FILTER CLOCK CONTROL

BACKGROUND OF THE INVENTION

1. Field of the Invention

The present invention generally relates to implantable medical devices, and more specifically, relates to sense amplifiers for implantable pulse generators.

2. Description of the Prior Art

Modern implantable pulse generators used in cardiac pacing commonly employ the demand or inhibited mode. In this technique the implantable pulse generator provides a pacing pulse only when a corresponding naturally occurring pacing pulse is not sensed within an appropriate period of time, called the escape interval. This sensing is normally accomplished by timesharing the wire or lead which conducts the pacing pulse from the implantable pulse generator to the cardiac tissue to be stimulated. The sensing activity is turned off whenever the lead is used to deliver a pacing pulse.

Many present day cardiac pacing implantable pulse generators both pace and sense in two chambers of the heart. That is both atrial and ventricular chambers are sensed for naturally occurring pacing pulses, and if not detected within the predetermined escape interval, an artificial pacing pulse is delivered to that chamber. Because of the characteristics of the artificial pacing pulses and the passband of the sense amplifiers, it is common to blank a sense amplifier during delivery of an artificial pacing pulse to another chamber. This is a particularly critical feature for the ventricular sense amplifier because of the relatively short interval between atrial and ventricular stimulation. This period of blanking is present on most modern dual chamber pulse generators.

The earliest demand pacers utilized analog sense amplifiers. These were implemented with discrete circuitry. As monolithic device technology became more available, attempts were made to manufacture monolithic sense amplifiers. The major difficulty was the need to use discrete resistors to implement R/C filters for the necessary bandpass filtering. The use of such discrete resistors added to the cost and complexity of the manufacturing processes.

A major breakthrough was made by Beck as described in U.S. Pat. No. 4,649,931. Beck applied switched capacitor circuitry to provide bandpass filtering in a pacing sense amplifier. This technique eliminates the use of resistors in the filtering circuit, relying instead on measuring the charge digitally switched into and out of an integrating capacitor.

A problem in bandpass filtering peculiar to the switched capacitor approach occurs if transients are present at a rate which interferes with the switching rate. This is not a problem when blanking a sense amplifier to time share the lead because the logic which generates a stimulation pulse can also compensate for these transients. Also the circuitry has almost an entire cardiac cycle to purge the transient from the system before sensing needs to begin.

The transient problem is most acute in the ventricular sense amplifier as a result of the period immediately following an artificial atrial pacing pulse. The difficulty is exacerbated by the relatively short time interval between atrial and ventricular contraction.

SUMMARY OF THE INVENTION

The present invention overcomes the problems associated with transients in the ventricular sense amplifier generated by an atrial pacing pulse in a switched capacitor ventricular sense amplifier. The basic solution is to change the clock rate for the switched capacitor sense amplifier during the period, immediately before, during and after an atrial paced event. This may be accomplished by stopping the clock entirely. With this approach, it is important to restart the clock again at the same phase as the stopping point to preserve the validity of the charge storage in the integrating capacitor.

An alternative approach is to greatly increase the clock rate to accomplish rapid processing of the transient during the blanked period With this approach, a gate must be used at the output of the sense amplifier to disable it during the processing of the transient.

BRIEF DESCRIPTION OF THE DRAWINGS

Further objects and advantages of the present invention will be apparent as the same becomes better known from the detailed specification and accompanying drawings in which like reference numerals refer to like components and wherein.

DETAILED DESCRIPTION OF THE PREFERRED EMBODIMENTS

The preferred modes of the present invention are assumed to be incorporated in a state-of-the-art implantable pulse generator for cardiac pacing However, those of skill in the art will be able to readily apply the teachings found herein to other applications requiring the processing of transients by a switched capacitor bandpass filter.

Figure 1:
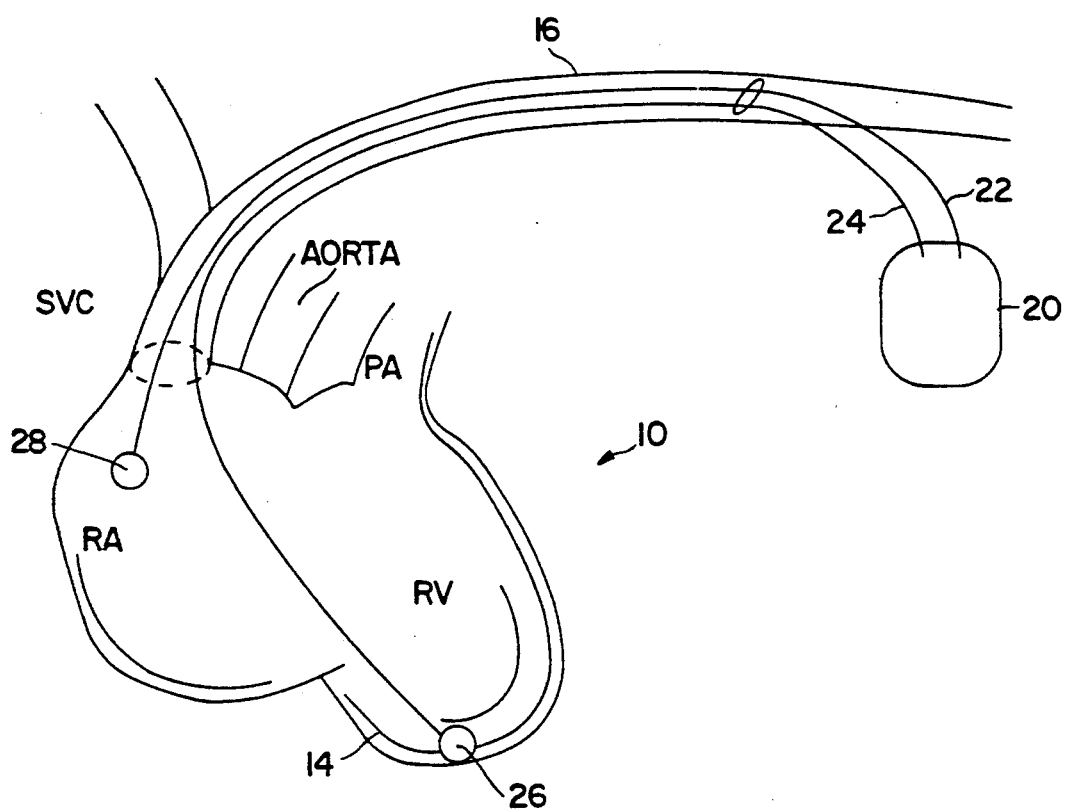
FIG. 1 is a schematic view of an implantable pulse generator employing the present invention in electrical contact with the heart of a patient.

FIG. 1 is a schematic view of a dual chamber implantable pulse generator used in cardiac pacing. The implantable pulse generator 20 contains the electronic circuitry to sense whether a naturally occurring contraction has been stimulated within the appropriate time, and if not, generate artificial pacing pulses. Because implantable pulse generator 20 senses and paces in both the atrium and the ventricle of the right heart, it must be electrically coupled to both chambers.

Transvenous pacing lead 22 is routed to right atrium 12 of heart 10 through the venous system 16. Transvenous pacing lead 22 makes electrical contact with the wall of right atrium 12 by electrode 28. Similarly, electrode 26 is in electrical contact with the wall of right ventricle 14 and is coupled to implantable pulse generator 20 via transvenous pacing lead 24.

The cardiac pacing system of FIG. 1 functions in the manner known in the art of dual chamber pacing systems.

Figure 2:
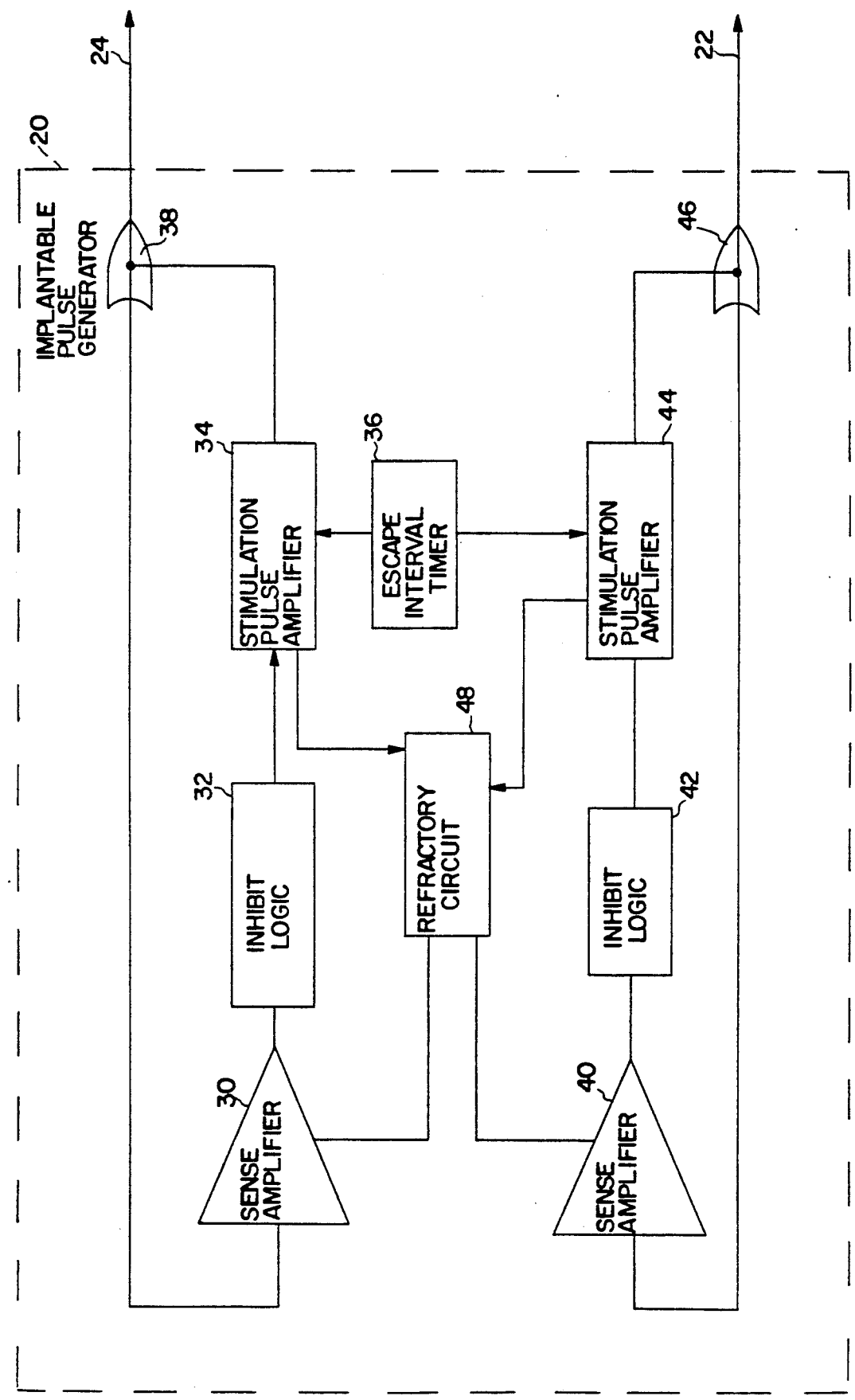
FIG. 2 is a block diagram of the circuitry of the implantable pulse generator.

FIG. 2 is a block diagram of the circuitry of implantable pulse generator 20. Transvenous pacing lead 24 electrically couples electrode 26 (see also FIG. 1) to wired-or 38 as shown If a naturally occurring contraction is electrically sensed by electrode 26, it is detected by sense amplifier 30. Inhibit logic 32 is notified of the detection, enabling it to inhibit generation of an artificial pacing pulse by stimulation pulse amplifier 34. If not inhibited by the time the escape interval has past, escape interval timer 36 notifies stimulation pulse amplifier 34 to generate an artificial ventricular pacing pulse which is transferred via transvenous pacing lead 24 to electrode 26. The atrial stimulation circuitry, comprising sense amplifier 40, inhibit logic 42, stimulation pulse amplifier 44, and wired-or 46 coupled to transvenous pacing lead 22, operates in similar fashion.

Refractory circuit 48 serves to decouple ventricular sense amplifier 30 from transvenous pacing lead 24 upon generation of an atrial pacing pulse by stimulation pulse amplifier 44 and a ventricular pacing pulse by stimulation pulse amplifier 34. Atrial sense amplifier 40 is similarly decoupled from transvenous pacing lead 22 upon generation of a ventricular pacing pulse by stimulation pulse amplifier 34 and an atrial pacing pulse by stimulation pulse amplifier 44.

Figure 3:
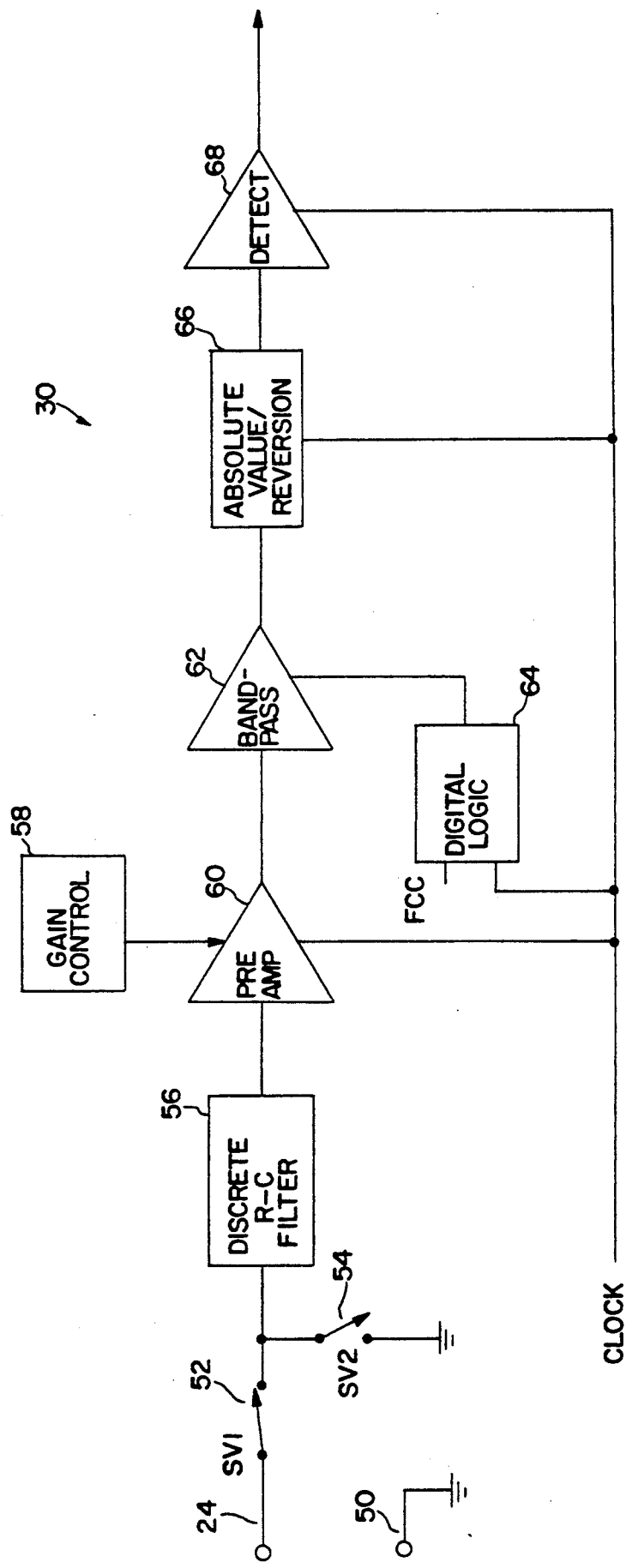
FIG. 3 is a block diagram of a ventricular sense amplifier employing the present invention.

FIG. 3 is a block diagram of ventricular sense amplifier 30 incorporating the present invention. Transvenous pacing lead 24 is electrically coupled to discrete R-C filter 56 through normally closed SPST switch 52. Notice that the input of discrete R-C filter 56 is also coupled to normally open SPST switch 54. Switch 52 and switch 54 serve to render sense amplifier 30 refractory to artificial atrial pacing pulses by opening switch 52 and closing switch 54 during the atrial pacing pulse (see also FIG. 2). This is necessary because the amplitude of the artificial atrial pacing pulse in the passband of sense amplifier 30 is so great as to saturate it for an unacceptable period. The output of discrete R-C filter 56 is amplified by preamp 60 with the gain of that amplification controlled by gain control 58.

The switched capacitor circuitry is distributed in preamp 60, absolute value/reversion 66, and detect 68 as well as in bandpass 62. The digital clocking of the band pass circuitry is controlled by digital logic 64. The clock input serves to synchronize the switched capacitor sense amplifier with the remainder of the circuitry of implantable pulse generator 20. Input FCC (i.e. filter clock control) notifies digital logic 64 of the period immediately preceding, during, and following the atrial paced event. These circuits are explained in greater detail below. Absolute value/reversion 66 and detect 68 serve to determine if a naturally occurring ventricular event has been identified.

Figure 4:
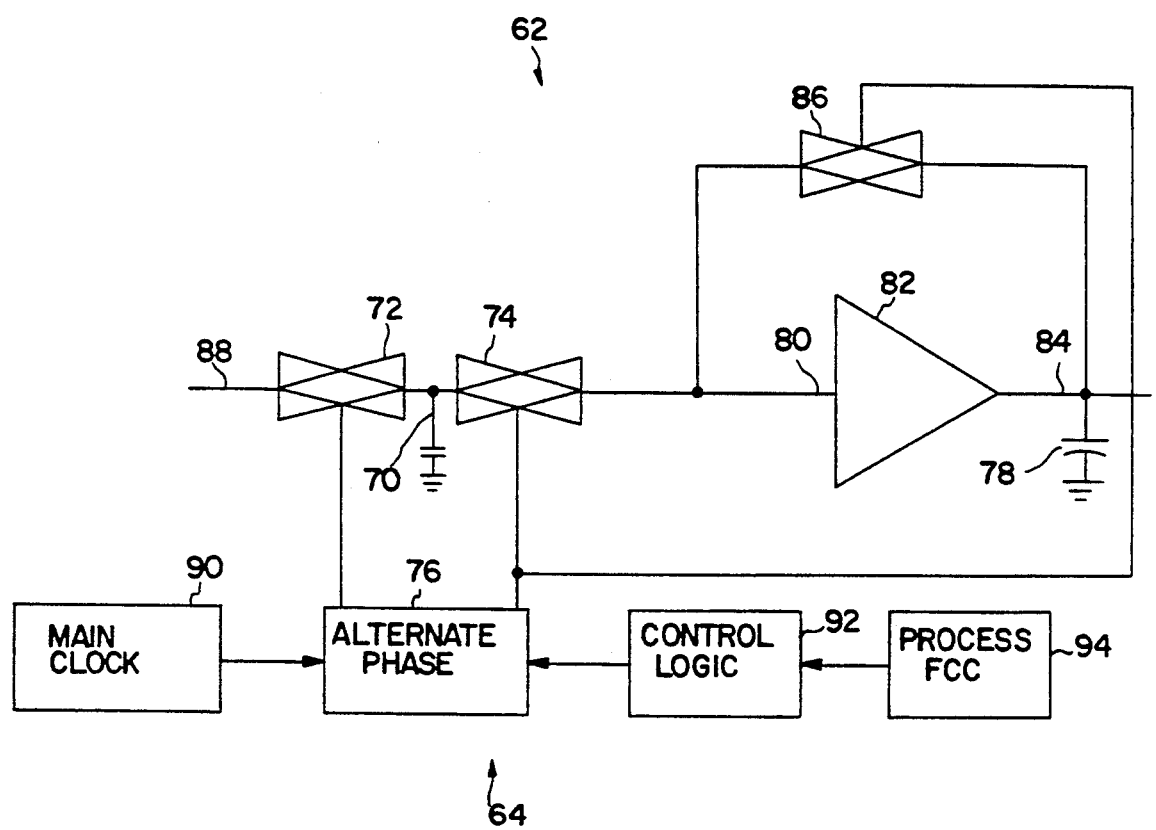
FIG. 4 is a detailed block diagram of the circuitry involved in the switched capacitor ventricular sense amplifier.

FIG. 4 is a block diagram showing the operation of bandpass 62 and digital logic 64. Digital logic 64 takes the output of main clock 90 and produces a two phase clock via alternate phase 76. The two outputs of alternate phase 76 are generated such that both outputs cannot be high at the same time. Process FCC 94 receives the FCC signal indicating the period immediately before, during and after the atrial paced event. Control logic 92 serves to disable the outputs of alternate phase 76 during this period. The outputs are restarted at the end of this period with the same clock phase which occurred when the period started.

The output 88 of preamp 60 (see also FIG. 3) is coupled to transmission gate 72 which is enabled by one output of alternate phase 76. When enabled, the current of output 88 charges storage capacitor 70. Only after transmission gate 72 is disabled, is transmission gate 74 enabled by the other output of alternate phase 76. This enables the charge of storage capacitor 70 to be applied to integrating capacitor 78 via amplifier 82. The effect of this differentiation at capacitor 70 and reintegration at capacitor 78 is to bandpass filter the signal of output 88 within a passband determined by the rate and pulse width of the outputs of alternate phase 76. A more detailed description of this process is available in U.S. Pat. No. 4,649,931 herein incorporated by reference.

The input to integrating capacitor 78 is a signal which is amplified by operational amplifier 82. The output 84 is the first stage of the bandpass filtered ventricular sense signal. Switchable network 86, controlled by the second output of alternate phase 76, provides a feedback network for operational amplifier 82.

Figure 5:
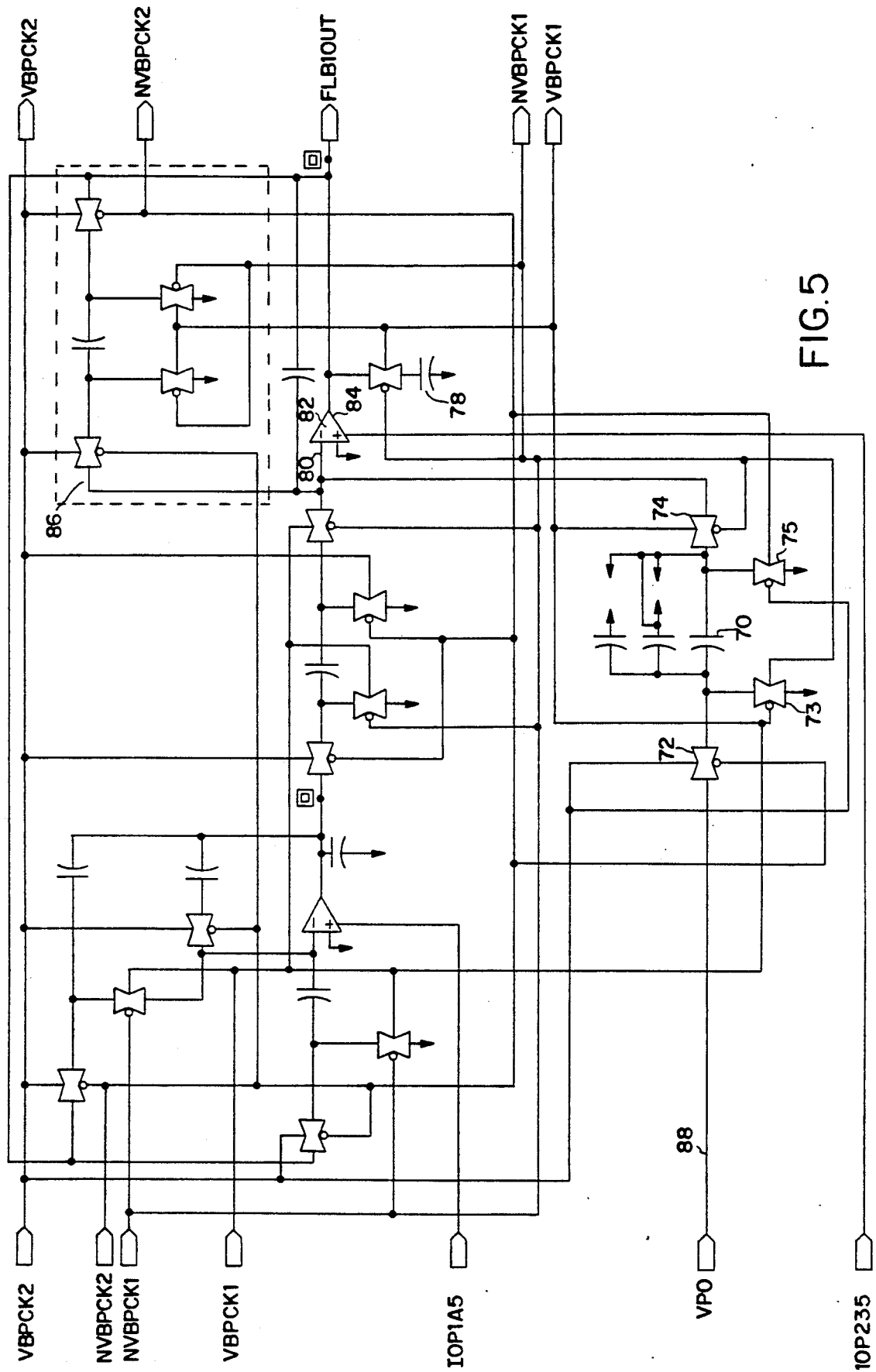
FIG. 5 is a schematic diagram of the circuitry of FIG. 4.

FIG. 5 is a detailed schematic diagram of a portion of the ventricular sense amplifier 30. Identified are the key components of bandpass 62 which have been described above. Transmission gate 75 is switched in phase with transmission gate 72 to complete the circuit for charging on the input of storage capacitor 70. Similarly, transmission gate 73 is switched in phase with transmission gate 74 to complete the circuit for output of storage capacitor 70.

Feedback network 86 provides feedback for amplifier 82. The network is switched permitting the network to bandpass limit the output also based upon the rate and pulse width of the input clock pulses.

Figure 6:
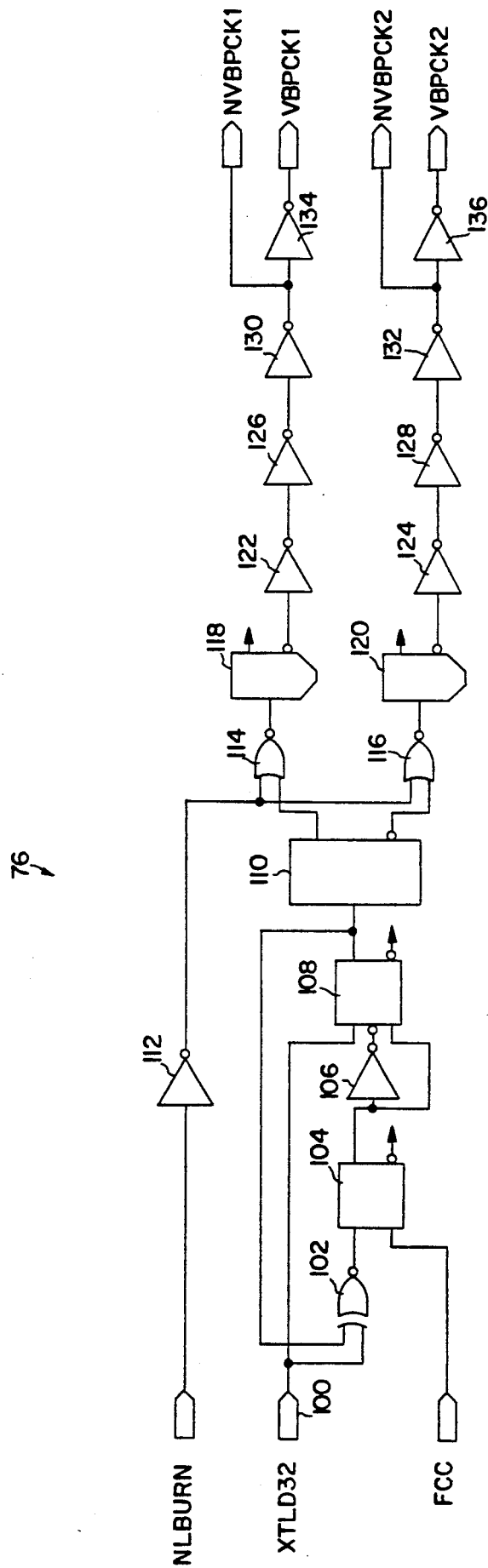
FIG. 6 is a schematic diagram of the circuitry of the switched capacitor clock.

FIG. 6 is a detailed schematic diagram of a portion of alternate phase 76. The main clock input is via input 100. This signal is divided into a two phase clock as discussed above. Notice that signal FCC (i.e., period immediately before, during and after an atrial paced event). holds set/reset latch 104 in the reset state. This effectively disables the output of alternate phase 76 during the period. Notice also that following the blanked period, the output of alternate phase 76 resumes at the same point as it stopped by simply removing the reset input of set/reset latch 104.

Figure 7:
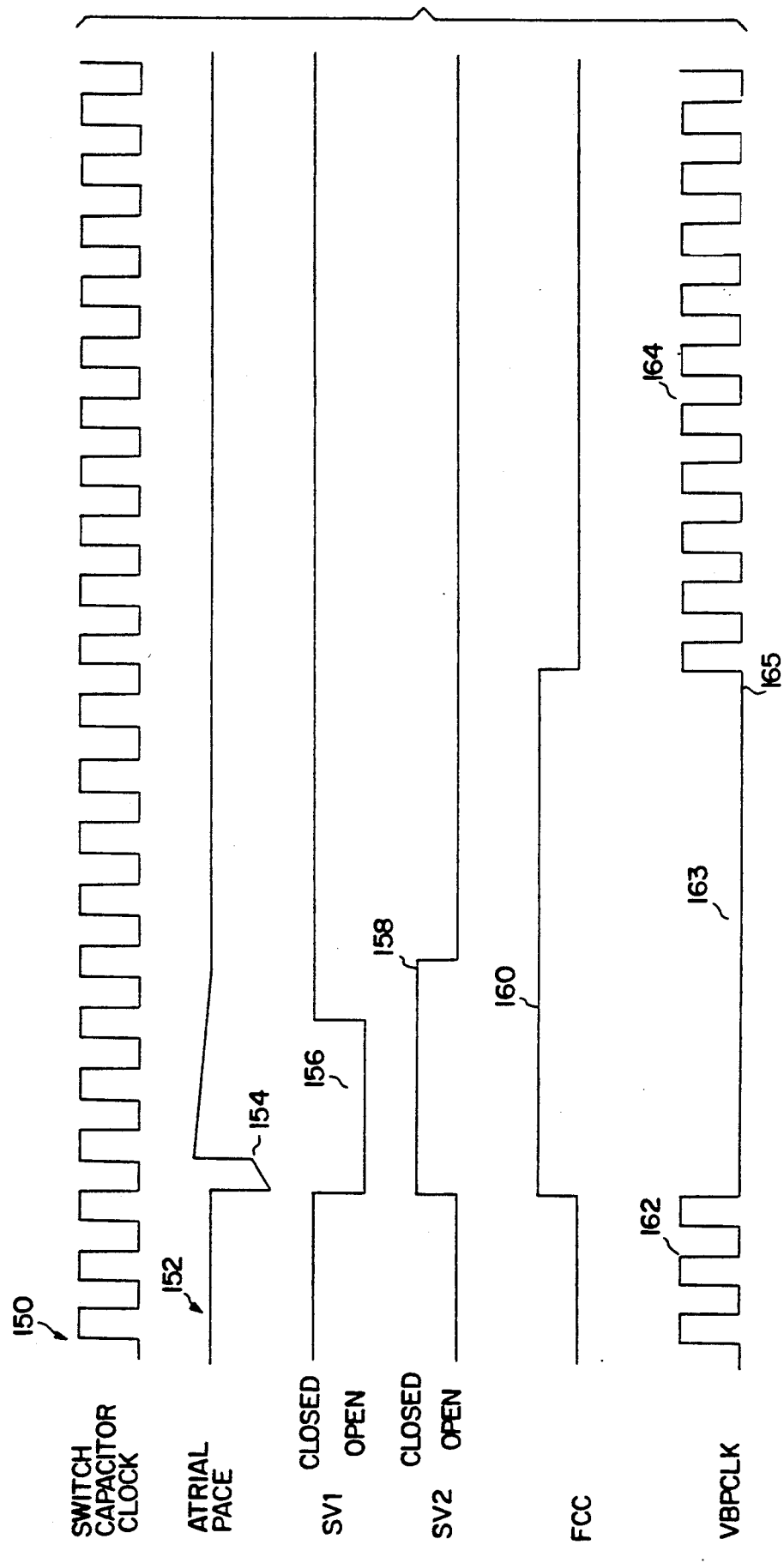
FIG. 7 is a timing diagram for a preferred embodiment of the present invention.

FIG. 7 is a timing diagram for the key signals of sense amplifier 30 employing the present invention. Signal 150 is the main clock input. It is constant over the observed period. Signal 152 is an atrial paced event as observed at transvenous pacing lead 22. The states of switches 52 and 54 are shown as signals 156 and 158, respectively (see also FIG. 3). Signal 160 is the filter clock control indicating the timing and duration of the blanked period.

Either output of alternate phase 76 is shown as signal 162 (the other output is similar but opposite in phase). During the blanked period 163, alternate phase 76 produces no output. The output 164 resumes after the blanked period is over. The output of alternate phase 76 maintains an exact (identical) phase relationship with signal 150 going into and going out of the static (frozen) state imposed by filter clock control signal 160.

Figure 8:
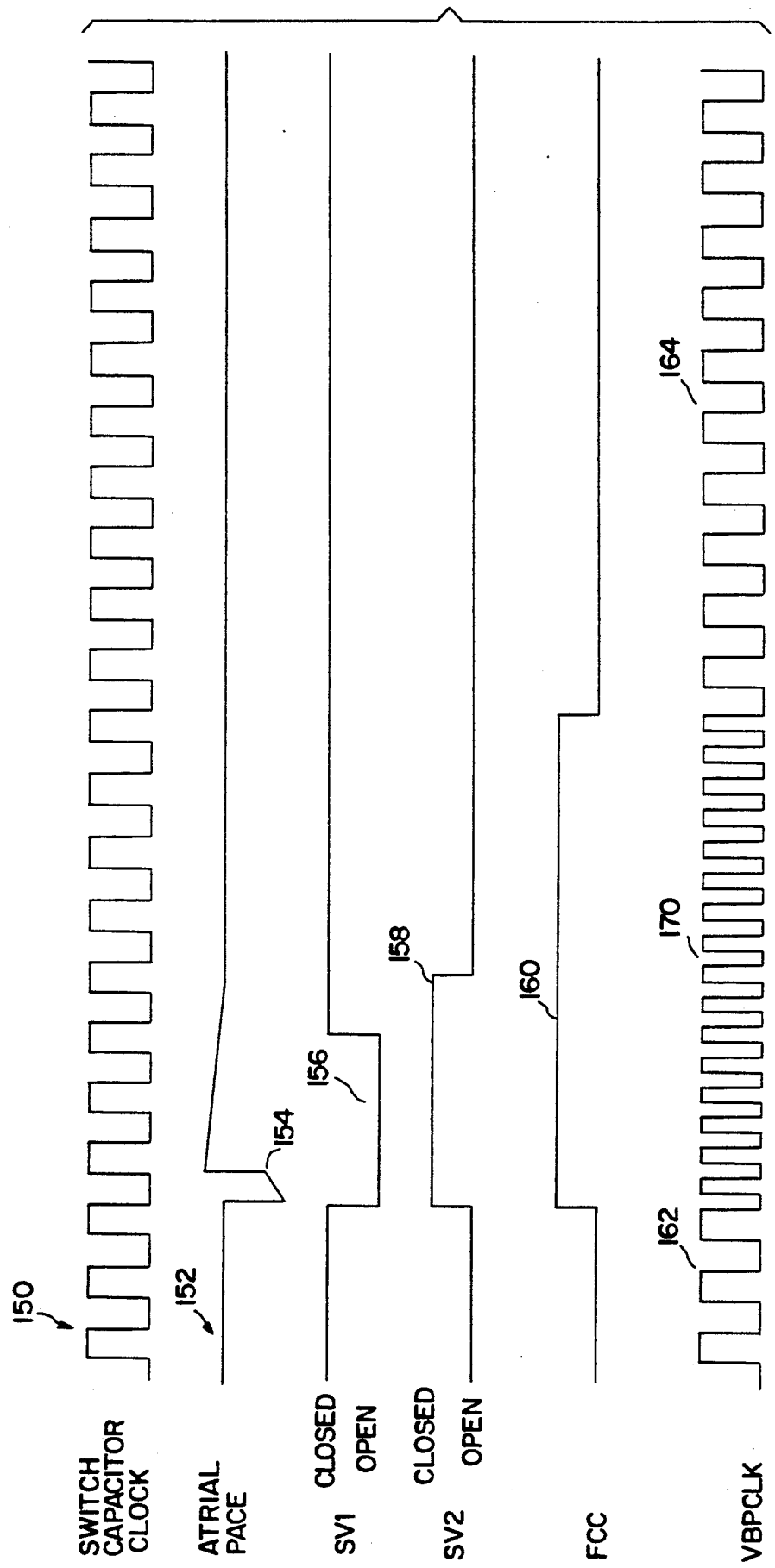
FIG. 8 is a timing diagram for an alternative embodiment of the present invention; and, FIG. 9 is a block diagram for an alternative embodiment of the present invention.

FIG. 8 is a similar timing diagram for an alternative embodiment of the present invention. The sole difference is that upon occurrence of the period immediately before, during and after an atrial paced event, high rate pulses 170 are generated. This ensures that the transients associated with the change of states of switches 52 and 54 are rapidly processed during the blanked period.

Figure 9:
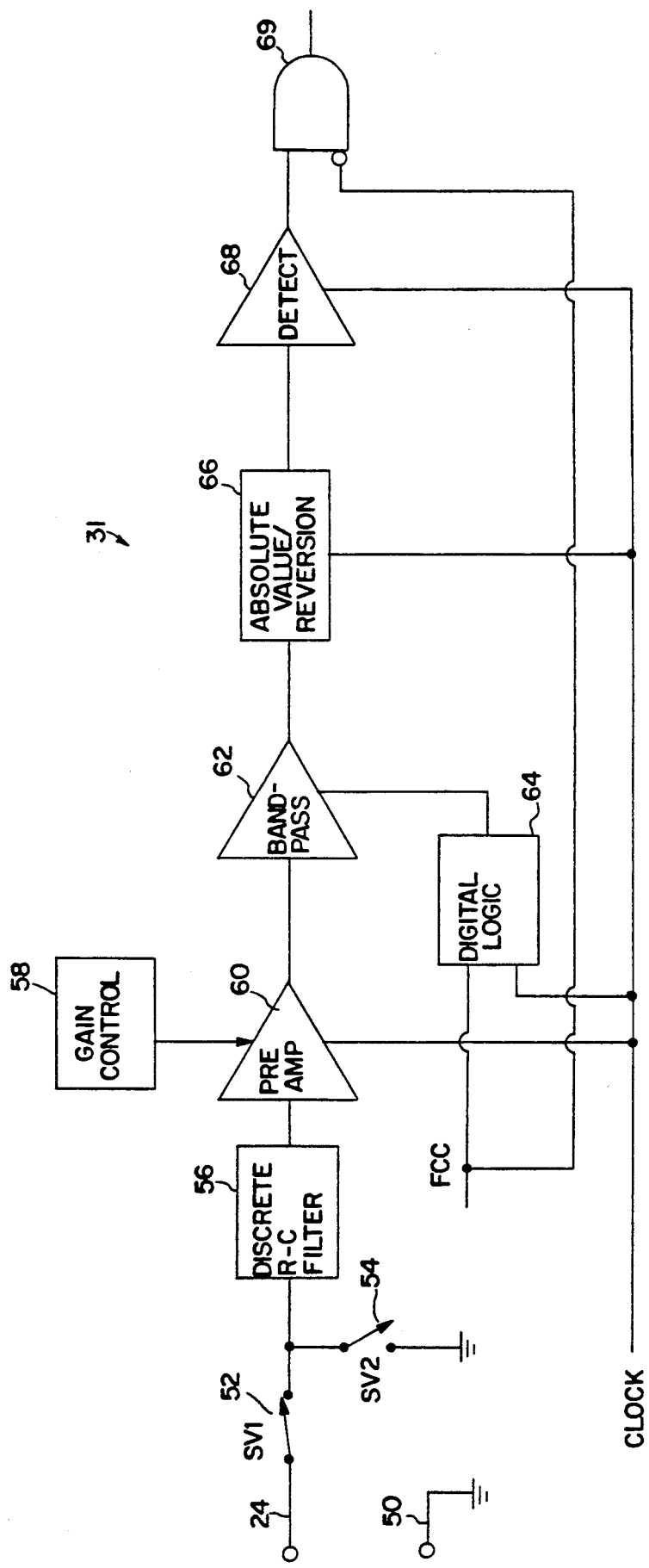

FIG. 9 is a block diagram of ventricular sense amplifier 31 employing an alternate embodiment of the present invention. Ventricular sense amplifier 31 operates according to the timing diagram of FIG. 8. Therefore, the transients associated with the blanked period are simply processed rapidly rather than being rejected. This necessitates the use of gate 69 which disables the output of ventricular sense amplifier 31 during the blanked period as controlled by FCC.

Having thus described the preferred mode of the present invention, those of skill in the art will be readily able to apply the teaching found herein to various other implantable devices without deviating from the scope of the claims hereto attached.

We claim:

1. A method of processing transients with a switched capacitor bandpass filter comprising:
   a. determining a time period likely to contain said transients;
   b. changing the rate of the clock of said switched capacitor bandpass filter to zero during said time period likely to contain said transients;
   c. restoring the rate of said clock to its initial rate, while preserving the phase of said clock with respect to the phase of said clock at said changing step, following said time period likely to contain said transients.

2. A method of processing transients with a switched capacitor bandpass filter comprising:
   a. determining a time period likely to contain said transients;
   b. increasing the clock rate of said switched capacitor bandpass filter during said time period likely to contain said transients;
   c. inhibiting the output of said switched capacitor bandpass filter during said time period likely to contain said transients; and
   d. restoring the clock rate to its initial rate following said time period likely to contain said transients and enabling the output of said switched capacitor bandpass filter following said time period likely to contain said transients.

3. An apparatus for bandpass filtering a signal and excluding transients, said apparatus having a filter output and further comprising:
   a. a clock having a first output and a second output wherein said first output and said second output are never on at the same time;
   b. a storage capacitor;
   c. a first switch coupled to said storage capacitor and responsive to said first output which couples said signal to said storage capacitor whenever said first switch is enabled by said first output;
   d. a second switch coupled to said storage capacitor and responsive to said second output which couples the contents of said storage capacitor to said filter output;
   e. means responsively coupled to said clock for increasing the rate of said clock during a time period likely to contain said transients; and
   f. means for disabling said filter output during said time period likely to contain said transients and for enabling said filter output following said time period likely to contain said transients.

4. An apparatus for bandpass filtering a signal and excluding transients said apparatus including a filter output and further comprising:
   a. a clock having a first output and a second output wherein said first output and said second output are never on at the same time;
   b. a storage capacitor
   c. a first switch coupled to said storage capacitor and responsive to said first output which couples said signal to said storage capacitor whenever said first switch is enabled by said first output;
   d. a second switch coupled to said storage capacitor and responsive to said second output which couples the outputs of said storage capacitor to a filter output;
   e. means responsively coupled to said clock for inhibiting said first output and said second output during said time period likely to contain said transients; and
   f. means for reinitiating said first output and said second output following said time period likely to contain said transients such that the phase state of said first and second outputs is preserved from the point at which said first and second outputs were inhibited.

5. In a cardiac pacemaker comprising means for generating stimulus pulses for application to one chamber of the heart and means for sensing electrical signals occurring in a second chamber of the heart, the improvement wherein:
   said means for sensing comprises a filter having a filter input for receiving electrical signals from said second chamber of the heart and a filter output, said filter comprising:
   a. a filter clock having a first output and a second output wherein said first output and said second output are never on at the same time;
   b. a storage capacitor;
   c. a first switch coupled to said storage capacitor and responsive to said first output, said first switch coupling sad filter input to said storage capacitor whenever said first switch is enabled by said first output;
   d. a second switch coupled to said storage capacitor and responsive to said second output, said second switch coupling the contents of said storage capacitor to said filter output;
   e. means responsively coupled to said filter clock for increasing the rate of said filter clock during a time period likely to contain said transients; and
   f. means for disabling said filter output during said time period likely to contain said transients.

6. In a cardiac pacemaker comprising means for generating stimulus pulses for application to one chamber of the heart and means for sensing electrical signals occurring in a second chamber of the heart, the improvement wherein:
   said means for sensing comprises a filter having a filter input for receiving electrical signals from said second chamber of the heart and a filter output, said filter comprising:
   a. a filter clock having a first output and a second output wherein said first output and said second output are never on at the same time;
   b. a storage capacitor;
   c. a first switch coupled to said storage capacitor and responsive to said first output, said first switch coupling said filter input to said storage capacitor whenever said first switch is enabled by said first output;

d. a second switch coupled to said storage capacitor and responsive to said second output, said second switch coupling the contents of said storage capacitor to said filter output;

e. means responsively coupled to said filter clock for inhibiting said first output and said second output during said time period likely to contain said transients and for reinitiating said first output and said second output following said time period likely to contain said transients such that the phase of said first and second outputs, when reinitiated is preserved from the phase of said first and second outputs, when inhibited.

* * * * *